(12) United States Patent
Mauuary (10) Patent No.: US 8,391,586 B2
(45) Date of Patent: Mar. 5, 2013

(54) METHOD AND INSTALLATION FOR INSPECTING A COILED STRIP

(75) Inventor: Stanislas Mauuary, Bonson (FR)

(73) Assignee: Siemens VAI Metals Technologies SAS, Saint Chamond (FR)

( * ) Notice: Subject to any disclaimer, the term of this patent is extended or adjusted under 35 U.S.C. 154(b) by 1168 days.

(21) Appl. No.: 12/293,908

(22) PCT Filed: Mar. 20, 2007

(86) PCT No.: PCT/FR2007/050971
§ 371 (c)(1),
(2), (4) Date: Oct. 21, 2008

(87) PCT Pub. No.: WO2007/107675
PCT Pub. Date: Sep. 27, 2007

(65) Prior Publication Data
US 2009/0208093 A1 Aug. 20, 2009

(30) Foreign Application Priority Data
Mar. 21, 2006 (FR) .................................... 06 50978

(51) Int. Cl.
*G06K 9/00* (2006.01)
(52) U.S. Cl. .......................................... 382/141; 156/64
(58) Field of Classification Search .................. 242/538, 242/538.2, 538.3; 382/141; 156/64, 379; 359/804
See application file for complete search history.

(56) References Cited

U.S. PATENT DOCUMENTS

| 2,502,469 | A | | 4/1950 | Martin |
| 2,771,251 | A | | 11/1956 | Silverstein |
| 2,930,228 | A | * | 3/1960 | Lawrence et al. ................ 73/159 |
| 4,234,135 | A | | 11/1980 | Conner, Jr. |
| 5,431,192 | A | | 7/1995 | Alexander, III |
| 7,500,502 | B2 | * | 3/2009 | Yamamoto et al. ........... 156/379 |
| 2005/0183521 | A1 | * | 8/2005 | Yamamoto et al. .......... 73/865.8 |

FOREIGN PATENT DOCUMENTS

| JP | 59113916 A | 6/1984 |
| JP | 8122274 A | 5/1996 |
| JP | 2000254725 A | 9/2000 |

* cited by examiner

*Primary Examiner* — Michael Mansen
*Assistant Examiner* — Juan Campos, Jr.
(74) *Attorney, Agent, or Firm* — Laurence A. Greenberg; Werner H. Stemer; Ralph E. Locher (57) ABSTRACT

A method and an installation are used for inspecting a surface of a coiled metal strip, wherein the coil to be inspected is unwound along a moving plane so as to cause at least part of the strip to move to a position for inspecting the surfaces. Accordingly, the method consists in moving the part of the strip to be inspected along a substantially vertical inspection plane, between an unwinding device and a winding device arranged on two vertically spaced apart levels on either side of an intermediate inspection level. Thus, the inspection is visually performed on both surfaces of the strip by an operator moving about on a floor at the intermediate inspection level.

12 Claims, 6 Drawing Sheets

METHOD AND INSTALLATION FOR INSPECTING A COILED STRIP

BACKGROUND OF THE INVENTION

Field of the Invention:

The object of the invention is a method and an installation for inspecting the two faces of a strip wound into a coil, in particular to check the quality of a sheet metal strip after lamination.

It is known that after the completion of lamination, the laminated sheet metal strip can show certain appearance defects which may be due, for example, to a slight variation in transversal thickness, resulting from the deformation and wear of the cylinders and/or the camber of the cage, or even to marks left by the working cylinders; certain defects may also be due to the support cylinders or to the cage itself.

These appearance defects appear on each face, in a longitudinal direction of lamination, with a period corresponding to the development, in this direction, of the circumference of the cylinders.

And yet it is increasingly necessary to deliver sheet metal which has a surface quality and generally as perfect an appearance as possible. To this end, it is therefore necessary to check the surface condition of the sheet metal strip after the completion of lamination, in particular, to observe the marks periodically left on the strip when passing between the working cylinders.

Taking into account the nature of the defects to detect, this inspection may be performed with difficulty using automatic means such as digital cameras which are used, for example, in hot rolling and it is preferable that the check be performed visually by an operator. For defects which are difficult to detect, a process known as "honing" has moreover been developed which consists of passing a special stone over the strip, using the inspection table for support.

Given that the lamination marks occur periodically, it suffices to perform the check on certain coils taken from the production circuit and only on a length of strip which corresponds to the largest period of marking on the various cylinders, which may be, for example, from 10 to 15 meters.

To this end, generally a section of strip is taken which forms a sufficiently long sample for the examination and which is transported to an inspection table.

Furthermore, it is necessary to observe the two faces of the strip and, after inspection of the upper face, it is necessary therefore to turn the strip over to check the other face.

In a described installation, for example, in document JP-2000 254 725, a sample is cut with a flying shear and sent to an inspection device placed downstream of the coiler and comprising several pairs of rollers between which the strip is clamped and which, when pivoting around a horizontal axis parallel to the side edge of the sample, allow the latter to turn over.

Another inspection device with turnover means, described in document JP 59 113 916, comprises a conveyor strip forming a mobile inspection table which, after the inspection of a first face, directs the strip towards a turnover device, possibly in two parts, comprising two conveyor strips between which the strip is clamped and which are carried by plates enabling a 180° rotation. The sample thus turned over is sent towards a second inspection table placed downstream thereof.

Given that, as has been shown, the sample taken from the strip must be sufficiently long, approximately 10 to 15 meters, such turnover devices are complex and expensive.

Moreover, the inspection is performed in conditions which can be quite uncomfortable for the operator, given that it is carried out on a strip laid flat.

BRIEF SUMMARY OF THE INVENTION

The object of the invention is a new inspection method and installation which enables all of these problems to be resolved without presenting the disadvantages of known installations.

In accordance with the invention, in order to inspect the two faces of a sheet metal strip wound into a coil, at least one section of the strip is unwound along an approximately vertical inspection plane between an unwinding device arranged at a first level, and a winding device arranged at a second level and the inspection is performed visually by an operator moving along a floor arranged at an intermediate level between the first and second level, and passing from one side to the other of the unwinding plane of the strip in order to inspect the two faces of the latter.

In a first embodiment, the coil is taken from the production circuit of a lamination installation for metal strips and rests on an unwinding device placed at a lower level, from which the coil is unwound by pulling one end of the strip which is fixed to a winding device placed at a higher level, so as to unwind a section to be inspected in front of the operator; the direction of unwinding is then reversed so that the inspected section can be rewound around the coil.

In another embodiment, the inspected strip is a sample of a laminated strip, wound into a reel which is arranged on an unwinding device placed at a first level and said reel is unwound in order that the sample is unwound in front of the operator, then rewound around a winding device placed at a second level.

If the strip is reverse laminated between two winding-unwinding devices placed on either side by at least one reversible lamination cage, the sample to be inspected can favorably be composed of the length of service coiled around one of the winding-unwinding devices, this length having undergone at least one lamination stage and therefore comprising marks left by the working cylinders and which are reproduced at each stage.

The invention also comprises an installation for inspecting both sides of a metal strip wound into a coil, comprising the means of control for unwinding the strip along an approximately vertical plane, between an unwinding device placed at a first level and on which the coil is placed, and a winding device placed at a second level and on which at least one section of the strip is wound in front of the inspection station placed on a floor at an intermediate level between the first and second level and on which an operator can move from one side of the unwinding plane of the strip to the other to enable the visual inspection of the two faces of said strip.

One particular advantage is that the installation comprises a detachable means of handling, which can be moved vertically between the first level to grip one end of the strip and the second level to engage said end on the winding device, then release it from the means of handling.

In a preferred embodiment, the means of handling are mounted on a movable carriage, along a winding plane of the strip, between two vertically separate positions, respectively, a first position at the first level, in the vicinity of the unwinding device, and a second position at a second level, in the vicinity of the winding device, said means of handling comprising two parts placed on either side of said unwinding plane of the strip and moving one towards the other so that one end of the strip is clamped in the unwinding plane.

Favorably, the means of handling comprise a supporting part, preferably a detaching ruler for the strip, fixed to the carriage, on one side of the unwinding plane of the strip and one mobile part placed on the other side of the unwinding plane which can be moved transversally to said plane in order to grip the end of the strip against the supporting part.

The invention thus enables the visual inspection of the two faces of the strip by unwinding said strip in front of an operator who can move along a floor placed at an intermediate inspection level, either side of the unwinding plane of the strip which passes through an opening in said floor.

According to another characteristic of the invention, the installation is equipped with at least one table placed at the inspection level and extending approximately along the unwinding plane of the strip over at least one side of the latter, said table being mounted on a frame which can be moved in parallel to said plane, between a separate position and an application position on the table of one corresponding face of the strip for the inspection of the opposite face by a honing process.

However, if the strip unwinds from a coil with a large diameter, it is possible to slow down the unwinding of the latter, so as to tension the strip enough in order to perform the honing test without using the table for support.

Other advantageous characteristics are set down in the following description of a particular embodiment, given as a non-restrictive example and illustrated by the appended diagrams, in which;

DESCRIPTION OF THE INVENTION

Figure 1:
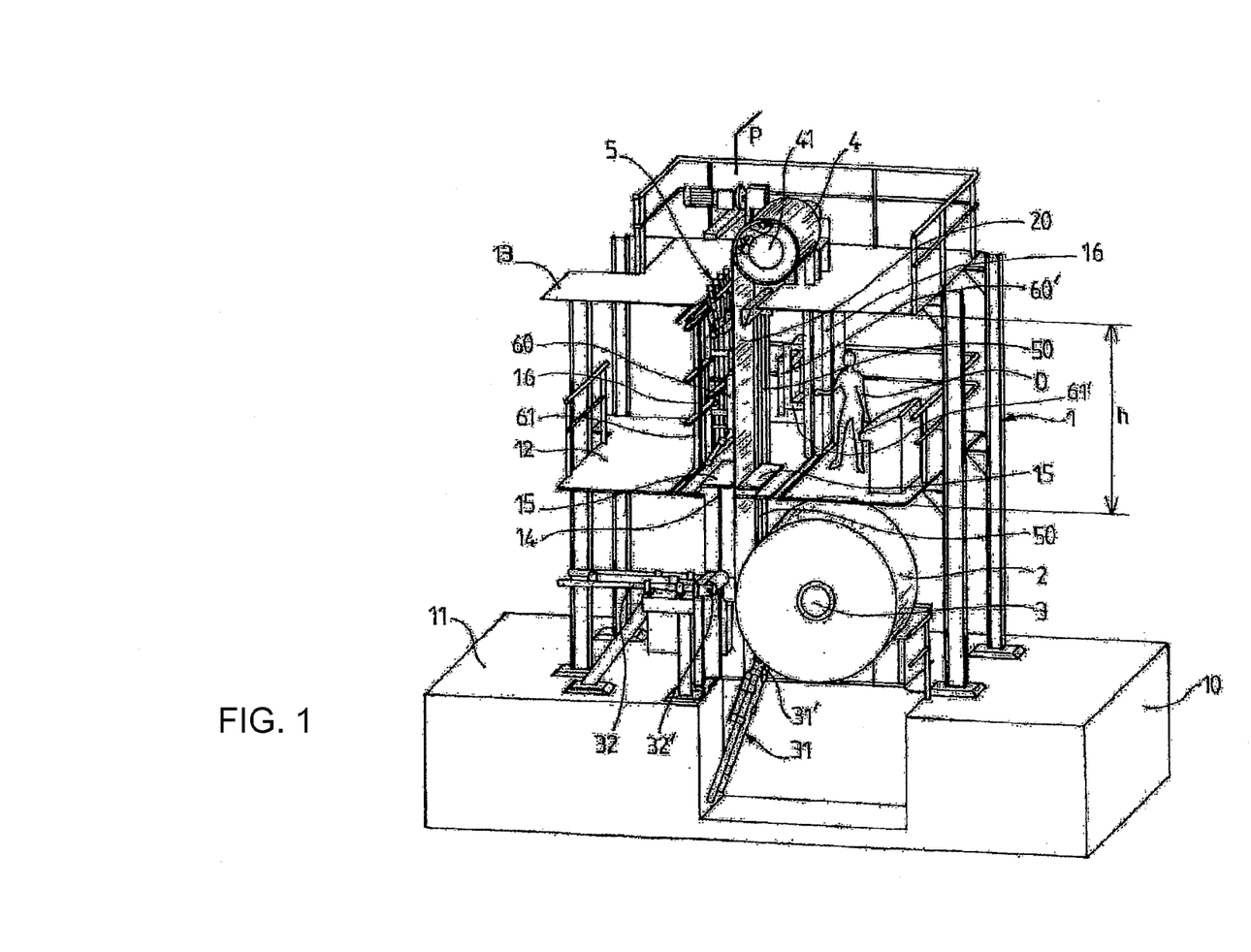
FIG. 1 shows a schematic perspective view of the entire installation in the inspection position.

FIG. 1 shows a schematic overview of an inspection installation according to the invention, placed inside a fixed frame 1 resting on a foundation block 10 and comprising, according to an essential characteristic of the invention, three superimposed levels, which are vertically separate, respectively a first lower level 11, a second upper level 13 and an intermediate level 12 where a floor is placed for the operator.

As a rule, to check the surface quality of the laminated strips, a coil 2 is taken from the production circuit, which is disposed on an unwinding device 3 fixed to the foundation block, that is to say, on the lower level 11 of the installation.

The strip 20 therefore unwinds from coil 2, in accordance with a vertical unwinding plane P, and winds around a winding device comprising a mandrel 4 placed on the upper level 13 of the frame 1 of the installation and rotated around a horizontal axis.

The unwinding device is represented simply on the diagrams, by a shaft 3 which is parallel to the unwinding plane P and on which the coil 2 is wound.

This shaft 3 is supported at both ends by a subframe which is not represented in the drawings, and preferably forms a sliding U-shaped frame which is horizontally mounted on the foundation block 10, in such a way as to support, during the unwinding of the coil, the last turn 22 of the latter, tangential to the vertical unwinding plane P.

The application means 31, 32 each comprising a roller 31', 32' mounted at the end of a telescopic arm actuated by jacks, enable the last turn 22 of the coil to be held during unwinding. The roller 31' can be rotated by means which are not represented, to control the rotation of the coil 2 on the shaft 3.

After the head 21 of the strip is detached, as described below, the application roller 32' rests on the coil 2 along a horizontal surface to enable the strip to unwind along the vertical plane tangential to this surface.

Figure 2:
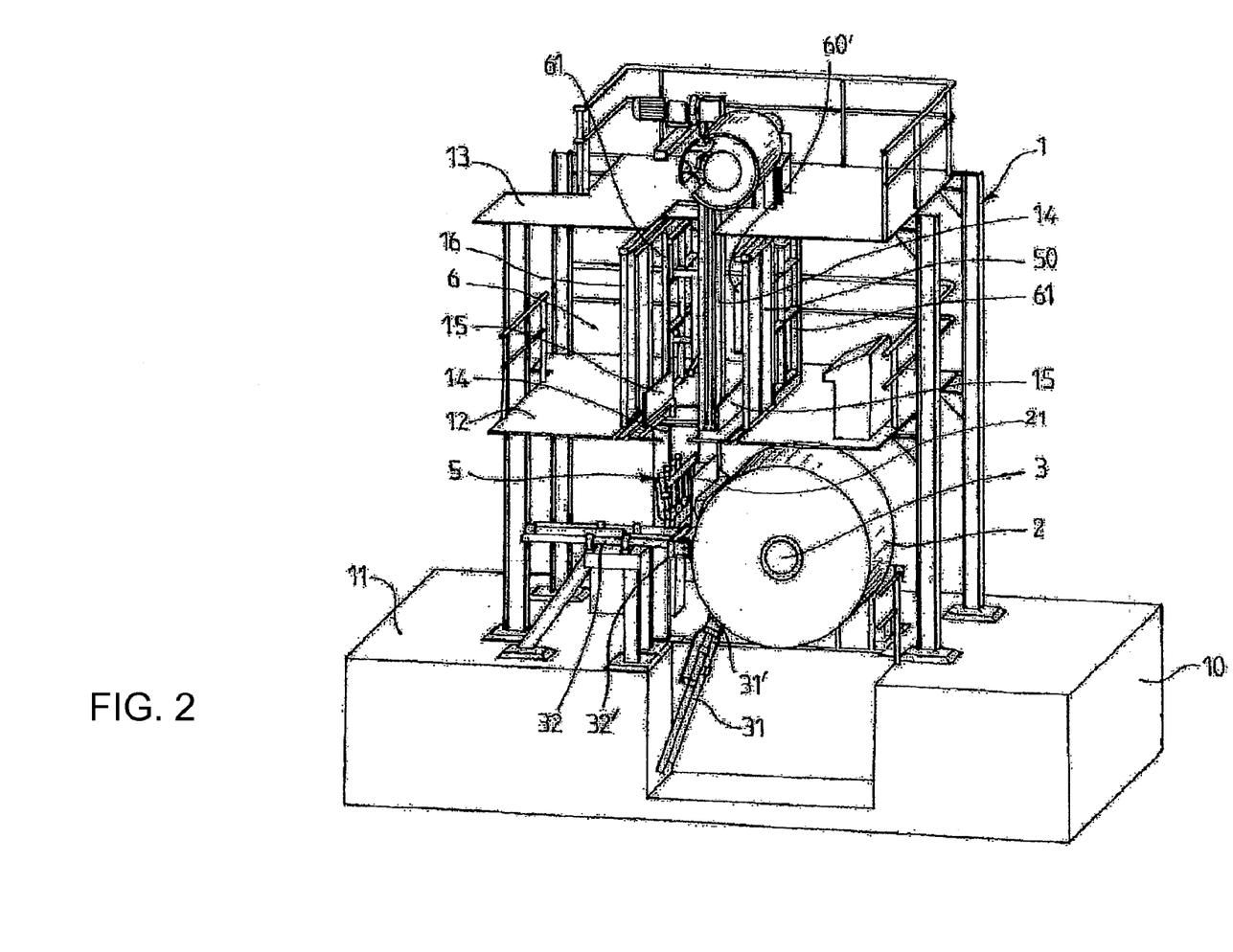
FIG. 2 shows the entire installation at the start of coil unwinding.
Figure 3:
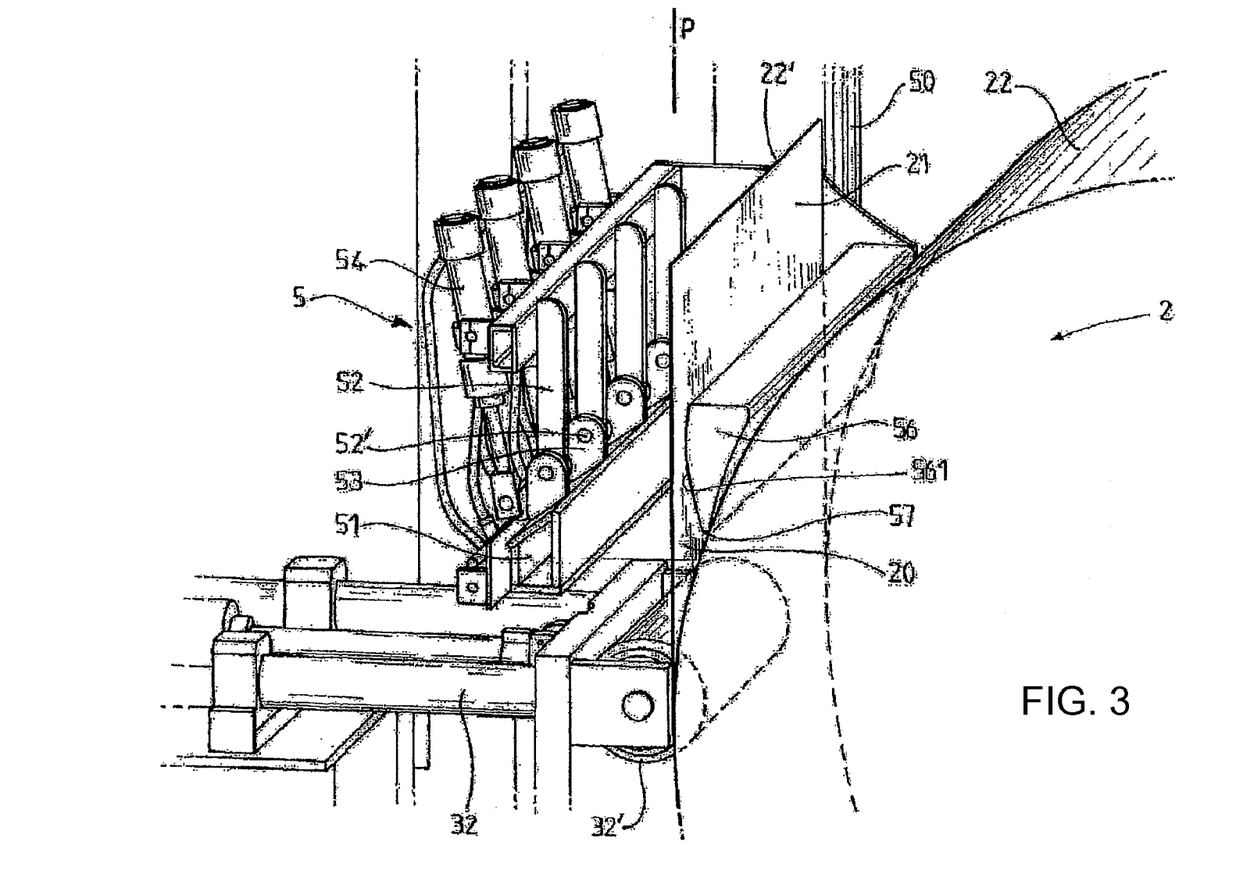
FIG. 3 shows a detailed view illustrating the means of handling in the lowered position.

As soon as the head 21 of the strip placed at the end of the last turn 22 becomes separate from the coil (FIG. 2), it engages in a handling component 5 represented in detail in FIG. 3 and mounted on a vertically movable carriage 51 and placed at this moment in the lowered position.

As shown in FIG. 3, the carriage 51 carries a plurality of levers 52 each articulated around an axis 52' on a yoke 53 mounted on the carriage 51 and each actuated respectively by a jack 54. The jacks 54 are controlled in synchrony in order to pivot the levers 52 simultaneously between a vertical position, represented in FIG. 3, which enables the passage of the head 21 of the strip 20, and a lowered position, represented in FIG. 4, against which each lever 52 rests, by a rounded end, on the strip 20 by clamping the head 21 of the latter against a ruler 56 placed on the opposite side and fixed at each end to the carriage 51. This ruler 56 has a transversal triangular cross-section with a crest 57 and two curved faces, respectively an external face 561 and an internal face 562 turned towards the coil 20.

Figure 4:
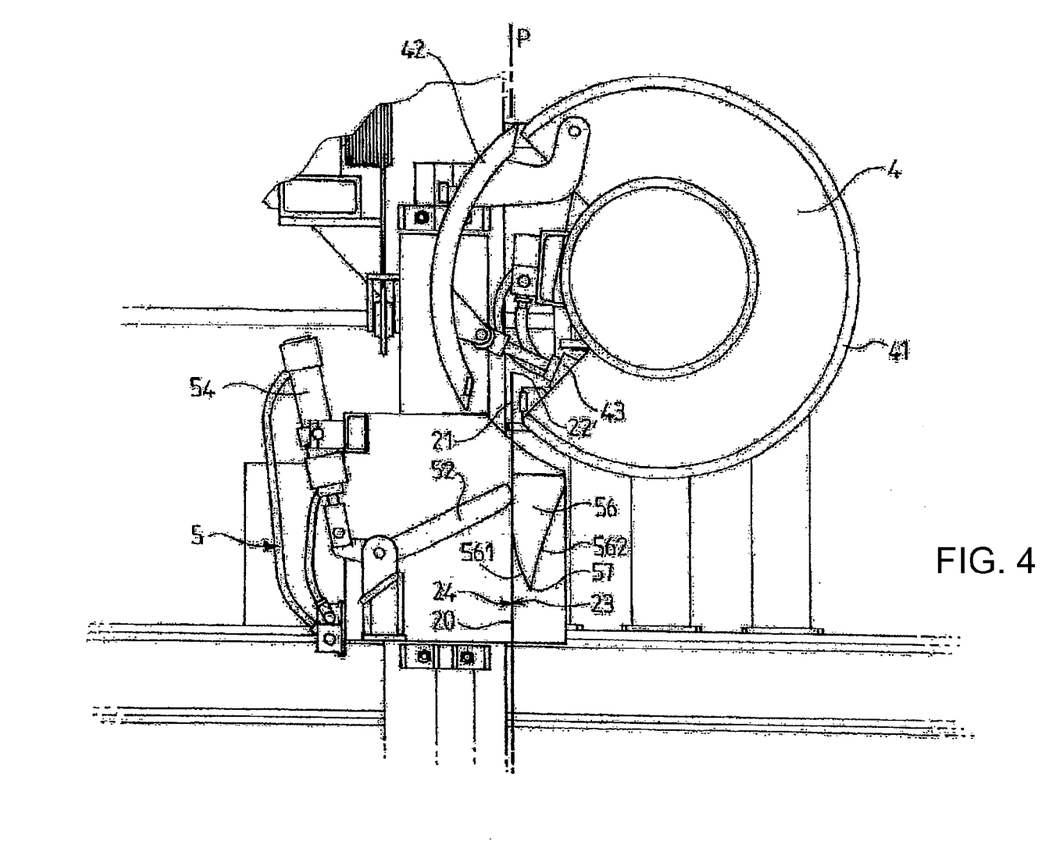
FIG. 4 shows a detailed view illustrating the means of handling in the raised position and the winding device.

Moreover, the carriage 5 is mounted such that it can slide along the vertical rails 50 on the frame 1, on both sides of the strip and it is actuated by a system which is not represented in order to move vertically between the lowered position, represented in FIG. 3, for handling the head 21 of the strip and a raised position, represented in FIG. 4, at the level of the upper floor 13 on which the winding device 4 is placed.

As indicated above, the shaft 3 on which the coil 2 is wound, is supported by a subframe (not represented) which is mounted so that it slides on the foundation block 2 such that, as the coil 20 unwinds, the external face 22 of the latter is maintained tangential to vertical plane P along which the external face 561 of the ruler 56 moves. This therefore forms a sort of knife having an edge 57 which, in the lowered position of the carriage 5 represented in FIG. 3, is positioned against the external face of the coil 20 which can be rotated by the application roller 31', the latter which may be motorized. In that way, the end 22' of the last turn 22 detaches along the stop 57 and the head 21 of the strip lifts between the external face 561 of the ruler 56 and the levers 52 which are then raised by the jacks 54 as shown in FIG. 3.

When the top edge 22' of the strip is located at an adequate height above the ruler 56, the levers 52 are lowered in such a way as to clamp the head 21 of the strip against the external face 561, the strip is then held in this way by the carriage 5. The vertical movement of the carriage 5, which determines the unwinding of the coil, is controlled by bringing the head 21 of the latter to the level of the winding device 4, in the position represented in FIG. 4.

This winding device comprises a cylindrical mandrel 41 mounted such that it rotates around a horizontal axis and comprises a cylindrical wall having an articulated part 42 which can pivot under the action of the jacks 43, in such a way as to house an opening in which the end 21 of the strip 20 can be engaged in the raised position of the carriage 5. The articulated part 42 is then closed by the jacks 43 on this end 21 of the strip and the mandrel 4 is rotated in order to control the winding of the strip 20 which unwinds from coil 2. Preferably, the unwinding of the coil is slowed down in order that strip 20 is maintained at a certain tension in the vertical unwinding plane P.

The strip thus runs across the intermediate floor 12 which passes above the coil 2 and is equipped with an opening 14 that is large enough to facilitate the passage of the carriage 5 with the strip. This opening can be closed after the passage of the carriage, by flaps 15 which simply leave a rectangular opening wide enough to prevent the strip from making contact with a fixed part.

The installation is then located in the position represented schematically in FIG. 1, in which a certain length of strip corresponding to the difference in level (h) between the floors 12 and 13 extends vertically in front of an inspection station 6 positioned on the intermediate floor 12. Thanks to the invention, this inspection can be performed visually by an operator O, the difference in levels h between the floors 12 and 13 being sufficient to enable the operator to move on the floor 12 by walking round the unwinding plane of the strip in order to observe directly either side of the two faces 23, 24.

On the other hand, the inspection table 6 may be equipped with various means of accessories which will be described now.

To guarantee safety during the operations, two vertical panels 16, parallel to the unwinding plane P, are mounted horizontally such that they slide between the two floors 12 and 13 and are only separated after the flaps 15 are closed in order to enable the two faces 23, 24 of the strip to be observed by the operator O.

Figure 5:
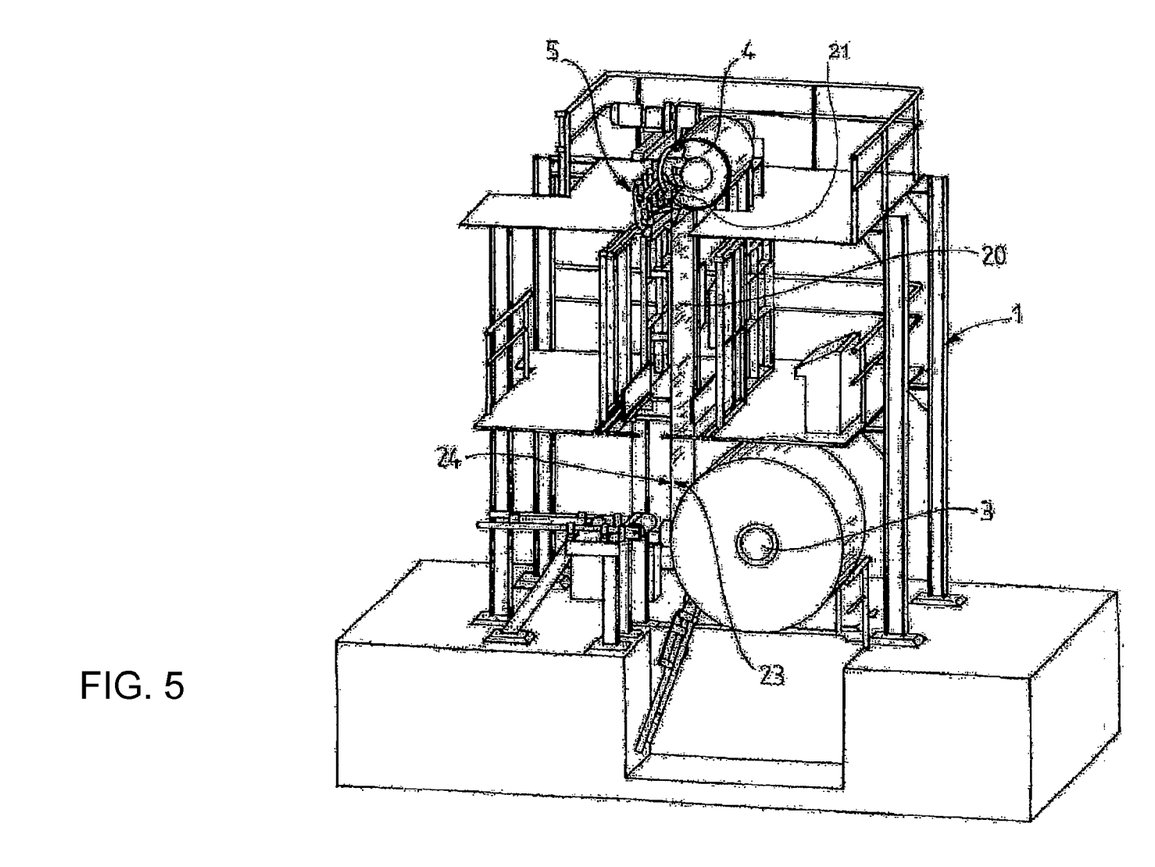
FIG. 5 shows an overview illustrating the mounting of the head of the strip on the winding device.

At the same time, on each side of the strip a vertical table 60, 60' is placed, supported by a frame 61, 61' which is also mounted horizontally so that it slides between the two floors 12 and 13, parallel to the unwinding plane P, in order to move between a separate position, represented in FIGS. 2 and 5, which enables, in particular, the passage of the carriage 5 with the strip 20 and an inspection position represented in FIG. 1, whereby the frame 61 placed on the opposite side of the inspected face 23, has been shifted such that the corresponding table 60 is located at a slight distance from the strip. When the flaps 15 are closed, the operator O can then move nearer the strip 20 and begin a honing inspection of the face 23 using the table 60 for support, by means of the opposite face 24 of the strip 20.

To prevent any risk of contact between the support table and the strip 20, the table 60 may be connected to the frame of the support 61, for example by a deformable parallelogram system which enables the table to move in parallel to itself between a separate position and an inspection position for which the table 60 is located almost in contact with the strip 20. This table 60 may, furthermore, be equipped with electromagnets to ensure the inspected part of the strip is positioned on the table 60, at the time of the inspection.

The operator O can thus visually inspect a first face 23 of the strip 20 and, possibly, perform honing using the table 60. This is then moved away again and the operator, moving around the floor 12, switches to the other side of the strip in order to inspect the other face 24. A second support table 60' can then be moved forward to come into contact with the strip 20 in order to perform the honing operation on the second face 24.

It is thus possible to visually inspect the two faces of the strip at a height which is slightly lower than the distance h between the intermediate floor 12 and the upper floor 13. As this height is, normally, lower than the desired inspection length, which depends on the period of marking of the cylinders by the rolling mill, the mandrel 4 is rotated in order to wind the inspected length to enable a new length of strip to reach the level of the inspection table. It is thus possible to inspect the necessary length, in stages, to identify the periodic defects due to cylinder marking.

The vertical inspection method, according to the invention, enables the period of the defects identified to be measured with precision, for example in the manner represented schematically in FIG. 6.

Figure 6A:
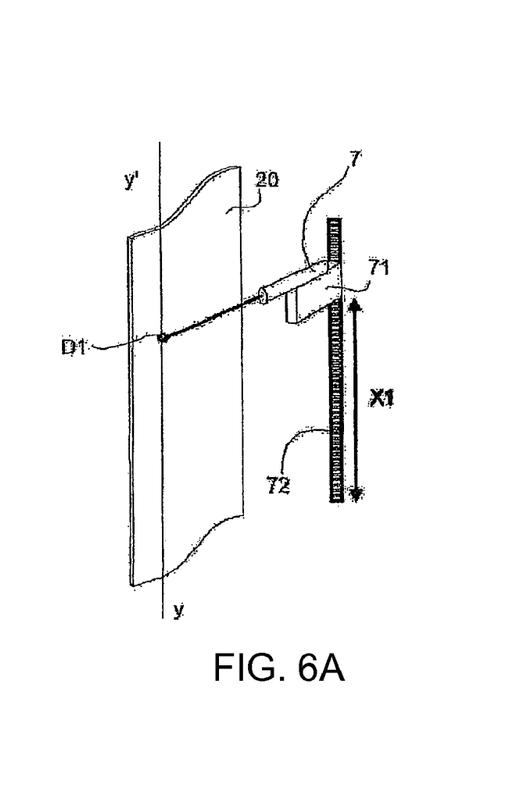
FIG. 6 shows, in three successive diagrams, the use of a laser viewfinder for identifying the lamination marks.
Figure 6B:
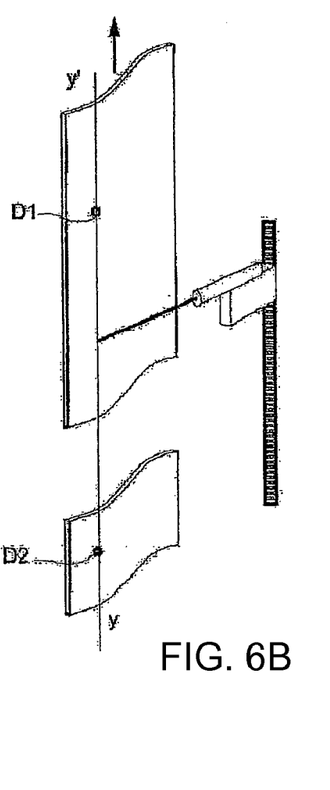
Figure 6C:
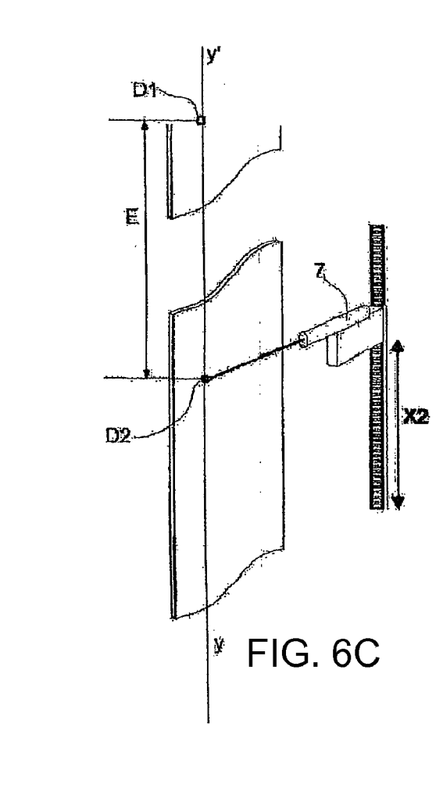

The inspection table 6 may in fact be equipped with a laser viewfinder 7 carried by a support 71 which is mounted such that it slides along a graduated ruler 72 which enables the position of the viewfinder 7 to be measured with precision. When the operator O has identified a defect D1 on the strip 20 which is stopped in the inspection position, he/she locates the position with precision using the viewfinder 7 (FIG. 6a). He/she then controls the rotation of the mandrel 4 to wind the inspected section (FIG. 6b) around the latter and sees a second defect D2 appear which, if it is placed on the same vertical line y'y as the first defect D1, corresponds most probably to a periodic marking. Winding of the strip is stopped again when the new defect D2 is located at the level of the operator. The operator then moves the viewfinder 7 to precisely locate the position of the second defect D2 (FIG. 6c). Knowing the rotation angle of the mandrel 4 between the two positions of FIGS. 6a and 6c and the diameter of the coiled turn, allows the coiled length L to be determined. The pitch E between the two periodic defects D1 and D2 is therefore:

$$E = L + (X1 - X2)$$

X1 and X2 being measurements of the two positions of the viewfinder 7 along the scale 72, respectively in the position 6a of the view of the first defect D1 and in the position 6c of the view of the second defect D2.

This pitch E can be determined by a computer which, having in its memory the characteristics of the rolling mill in which the inspected coil was handled, in particular the diameter of the cylinders and the thickness reduction rate in each cage, can give an indication about the origin of the defects detected, in particular the cylinders having caused periodic marking in order to, for example, identify the cylinders to be replaced or adjusted.

The invention is naturally not restricted to the details of the embodiment which is given as a simple example but, on the contrary, covers all of the variants within the same framework of protection and using, notably, equivalent means.

In particular, the invention is designed especially for the visual identification of marks resulting from lamination in order to make the necessary corrections, but would also enable other defects to be identified and, generally, the surface quality of a sheet metal strip to be checked.

Furthermore, other means for controlling the winding and unwinding of the strip could be used. In the same way, the inspection table could be positioned differently, and other means of inspection could be used.

For example, as indicated above, it is possible to tension the strip between the winding mandrel 4 and the coil 2 whose unwinding is curbed. This tension could be sufficient to perform the inspection by the honing process, without pressing the strip against the vertical tables 60, 60' which may therefore be eliminated.

Moreover, in the described embodiment, the inspection is performed on certain coils taken from the production circuit and transported to a separate installation where the coil is unwound on a horizontal table. It is therefore only possible to inspect the upper face of the strip and, to check the two faces, it is generally preferable to take a sample of the strip having the necessary length, that is to say, approximately 10 to 15 m. Thus, this sample can be turned over to successively inspect the two faces.

In the described known arrangement, for example, in document JP-2000 254725, this sample is cut by a flying shear and sent by shunting to the inspection table which is positioned immediately downstream from the winder. However, the assembly is very bulky and there is not always enough space, in particular for modernizing an existing installation.

The arrangement of document JP 59 113916 is even more bulky as it provides for positioning a turnover device between the two inspection tables.

On the other hand, the installation according to the invention is considerably less bulky, whilst enabling the visual inspection of two faces, given the fact that this inspection is performed along a vertical plane.

In the case of a continuous laminating installation comprising two winders placed one after the other or mounted on a carousel for example, the inspection installation may be placed immediately near to the rolling mill output, next to the winders or immediately downstream of the latter. At the end of the winding process, the coil must then only be moved a few meters for it to be in the unwinding position, at the lower part of the inspection installation. It is therefore unnecessary to transport the coil in a separate installation.

However, the arrangement according to the invention also represents the advantages of inspecting a sample.

In this case, it is possible to wind this sample into a reel which, having a sufficiently reduced length, less than 20 m, may easily be transported in an inspection installation comprising an unwinding device and a winding device placed, respectively, at two separate height levels. From the unwinding device placed at a first level which is not necessarily the lower level, the strip unwinds vertically in front of the operator to wind around the winding device placed at a second level. The new reel thus formed in this way can then be discharged without it being necessary to unwind it in the opposite direction to rewind it.

Furthermore, such a process could also be used to check the surface quality of a strip laminated on both sides in at least one cage placed between the two winding-unwinding devices. It is known that, in this case, to maintain the tension of the strip during lamination, it is necessary to maintain a coiled length of service on each of the winding-unwinding devices. This length of service has only been laminated during the first passage of the strip and must therefore be discarded but it comprises periodic lamination marks and can therefore be used as a sample to identify defects. This length of service can therefore be wound into a reel which is subject to a vertical inspection as described above.

It therefore appears that the invention provides for multiple applications and can adapt to very different situations, in particular for the modernization of existing installations.

The invention claimed is:

1. A method for inspecting two faces of a metal strip wound into a coil, which comprises the steps of:
    unwinding at least one section of the metal strip along an inspection plane extending approximately vertically between an unwinding device disposed at a first level with respect to a ground surface and a winding device disposed at a second level with respect to the ground surface; and
    performing an inspection visually by an operator moving along a floor disposed at an intermediate level between the first level and the second level and the operator being able to move from one side to the other of the inspection plane of the metal strip to inspect the two faces of the metal strip.

2. The method for inspecting according to claim 1, which further comprises:
    taking a coil from a production circuit of a lamination installation for metal strips and disposing the coil on the unwinding device placed at a lower level being the first level;
    pulling one end of the metal strip resulting in an unwinding of the coil and fixing the one end on the winding device placed at a higher level being the second level; and
    unwinding a section to be inspected in front of the operator and that a direction of unwinding is reversed to rewind an inspected section around the coil.

3. The method for inspecting according to claim 1, wherein an inspected strip is a sample of a laminated strip, wound into a reel which is disposed on the unwinding device placed at the first level and that the reel is unwound to unwind the sample in front of the operator and also then wound on the winding device placed on the second level.

4. The method for inspecting according to claim 3, wherein given that the metal strip is reverse laminated between two winding-unwinding devices, the sample to be inspected is a length of service coiled around one of the winding-unwinding devices and having undergone at least one lamination process.

5. The method for inspecting according to claim 1, which further comprises for inspecting a face of the metal strip, applying the other face of the metal strip to a table extending along an approximately vertical direction and being able to move between an inspection position in the unwinding plane and a separate position.

6. An inspection installation for inspecting two faces of a metal strip wound around a coil, the inspection installation comprising:
    a first level with respect to a ground surface;
    a second level with respect to the ground surface;
    a winding device disposed on said second level;
    an unwinding device disposed on said first level and on which the coil is placed;
    an intermediate level having a floor and disposed between said first and second levels;
    an inspection station disposed on said floor of said intermediate level; and
    an approximately vertical inspection plane extending approximately vertically between said unwinding device disposed on said first level and said winding device disposed on said second level, and on said winding device at least one section of the metal strip winds by unwinding in front of said inspection station disposed on said intermediate level, and on said intermediate level an operator can move by passing from one side to the other side of the vertical plane being an unwinding plane for visually inspecting the two faces of the metal strip.

7. The inspection installation according to claim 6, further comprising detachable means for handling the metal strip, said detachable means for handling moving vertically between said first level, where said detachable means for handling grabs one end of the metal strip, and said second level where said one end attaches to said winding device and then said detachable means for handling releases said one end.

8. The inspection installation according to claim 7,
further comprising a carriage, said detachable means for handling being mounted on said carriage, said carriage being moved along the approximately vertical inspection plane of the metal strip, between two vertically separate positions, one near said unwinding device on said first level and the other, near said winding device on said second level; and
wherein said detachable means for handling contains two parts placed respectively on either side of the unwinding plane of the metal strip and a means for moving one of said two parts towards the other to clamp the one end of the metal strip and maintain the metal strip in the unwinding plane during vertical movement of said carriage.

9. The inspection installation according to claim 8, wherein said two parts include a supporting part mounted fixedly on said carriage, on a same side as the coil in relation to the unwinding plane and a mobile part placed on the other side of the unwinding plane and said mobile part can be moved transversally to the unwinding plane to clamp the one end of the metal strip against said supporting part.

10. The inspection installation according to claim 9, wherein:
   said supporting part of said detachable means for handling is a horizontal ruler having a stop for detaching the one end of the metal strip; and
   said mobile part has at least one arm mounted such that said at least one arm pivots on said carriage and is actuated by said means for moving being a jack between a separate position and a position for clamping the one end of the metal strip on said horizontal ruler.

11. The inspection installation according to claim 7, wherein said winding device contains a clamping component for engaging a head of the metal strip passing above said detachable means for handling.

12. The inspection device according to claim 11, wherein said inspection station has a frame and at least one table extending along the unwinding plane, on at least one side of unwinding plane, said table being mounted on said frame which can be moved parallel to the unwinding plane, between a separate position and an application position on said table of a corresponding face of the metal strip to inspect the other face by a honing process.

* * * * *